US010117768B1

(12) United States Patent
Freed et al.

(10) Patent No.: US 10,117,768 B1
(45) Date of Patent: Nov. 6, 2018

(54) CERVICAL TRACTION COLLAR

(71) Applicants: William L. Freed, Trumbull, CT (US); Matthew W. Freed, Trumbull, CT (US)

(72) Inventors: William L. Freed, Trumbull, CT (US); Matthew W. Freed, Trumbull, CT (US)

( * ) Notice: Subject to any disclaimer, the term of this patent is extended or adjusted under 35 U.S.C. 154(b) by 421 days.

(21) Appl. No.: 14/528,685

(22) Filed: Oct. 30, 2014

Related U.S. Application Data

(60) Provisional application No. 61/897,282, filed on Oct. 30, 2013.

(51) Int. Cl.
*A61F 5/055* (2006.01)
*A61F 5/01* (2006.01)

(52) U.S. Cl.
CPC .............. *A61F 5/012* (2013.01); *A61F 5/055* (2013.01); *A61F 2250/0003* (2013.01)

(58) Field of Classification Search
CPC .. A61F 5/012; A61F 5/04; A61F 5/042; A61F 5/05; A61F 5/055; A61F 5/05816; A61F 5/05883
USPC ..................................................... 602/13, 18
See application file for complete search history.

(56) References Cited

U.S. PATENT DOCUMENTS

| | | | |
|---|---|---|---|
| 4,708,129 A * | 11/1987 | Pujals, Jr. ............... | A61F 5/055 128/DIG. 23 |
| 5,403,266 A | 4/1995 | Bragg et al. | |
| 7,670,307 B2 * | 3/2010 | Chitwood ............ | A61H 1/0296 128/869 |
| 7,981,068 B2 * | 7/2011 | Thorgilsdottir ......... | A61F 5/055 128/846 |

* cited by examiner

*Primary Examiner* — Keri J Nelson
(74) *Attorney, Agent, or Firm* — Perman & Green, LLP

(57) ABSTRACT

In accordance with one or more aspects of the disclosed embodiment, a cervical collar includes a semi-rigid collar substantially conforming to the back of a neck, an occipital locking mechanism coupled to the semi-rigid collar, configured to generally conform to and engage with the base of a skull at the occipital or mastoid region without engaging the temporomandibular joint, jaw or chin of the skull and a traction mechanism coupled to the semi-rigid collar, the at least one traction mechanism configured to provide cervical traction through the occipital locking mechanism of the semi-rigid collar against the base of the skull without pressure against the temporomandibular joint, jaw and chin.

23 Claims, 8 Drawing Sheets

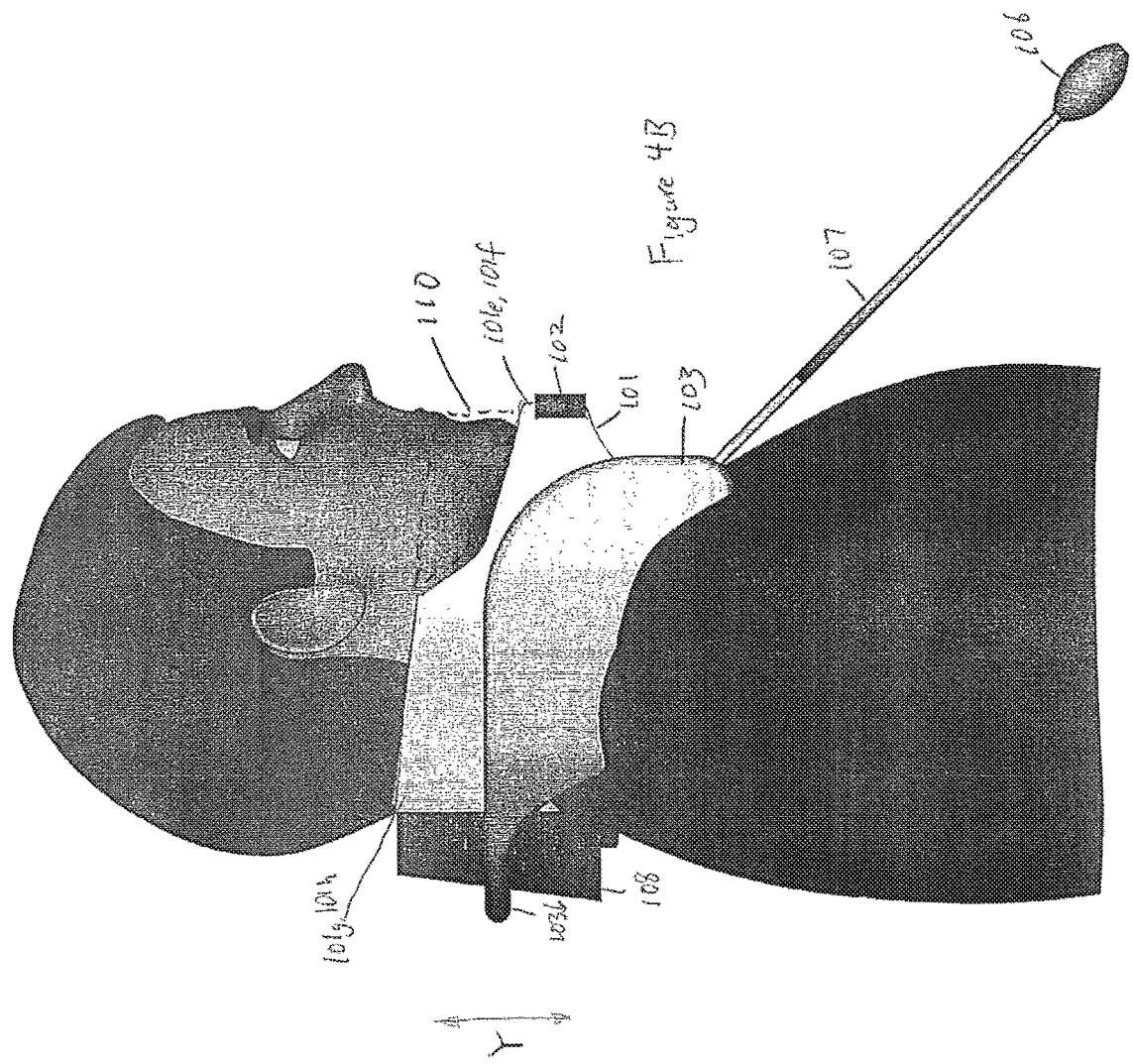

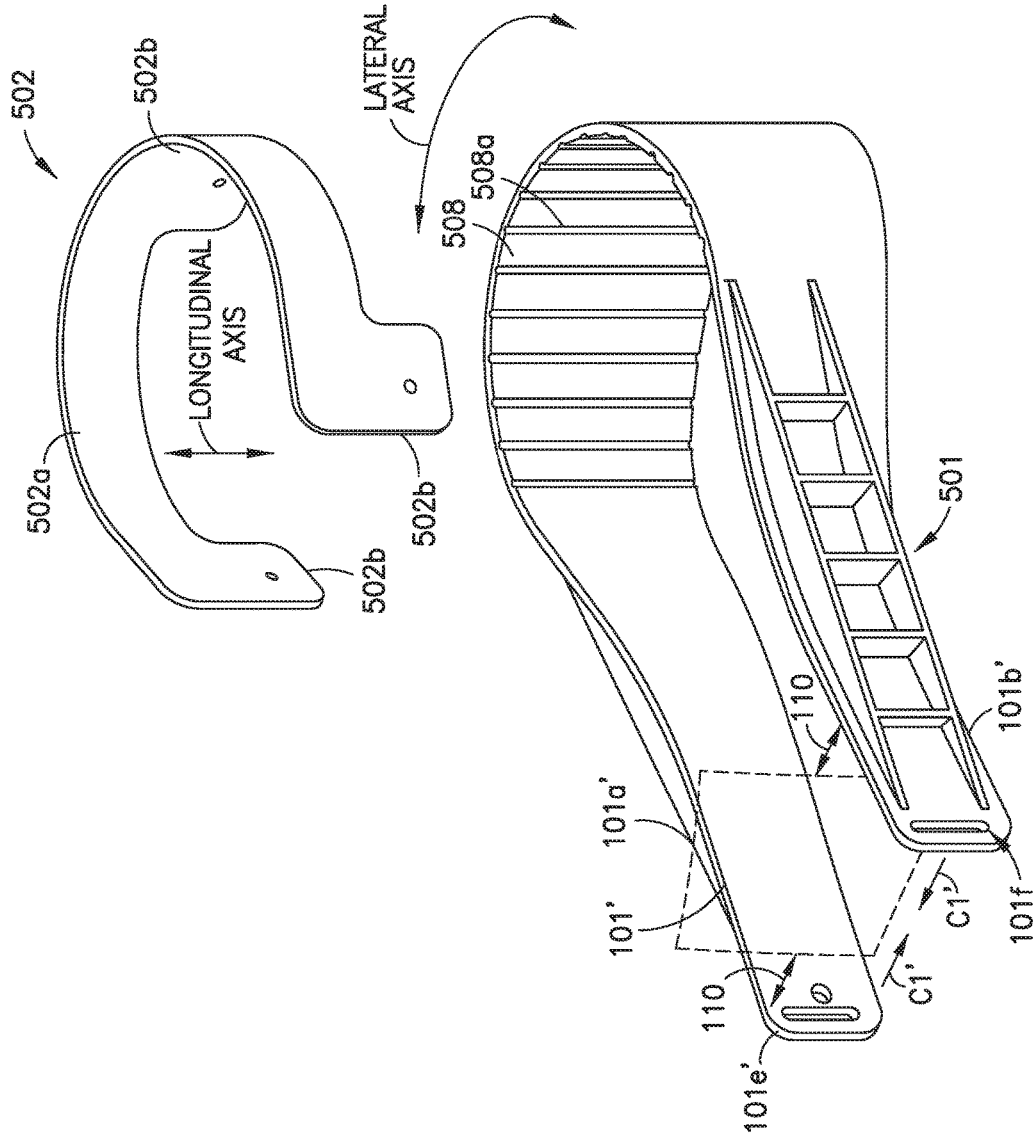

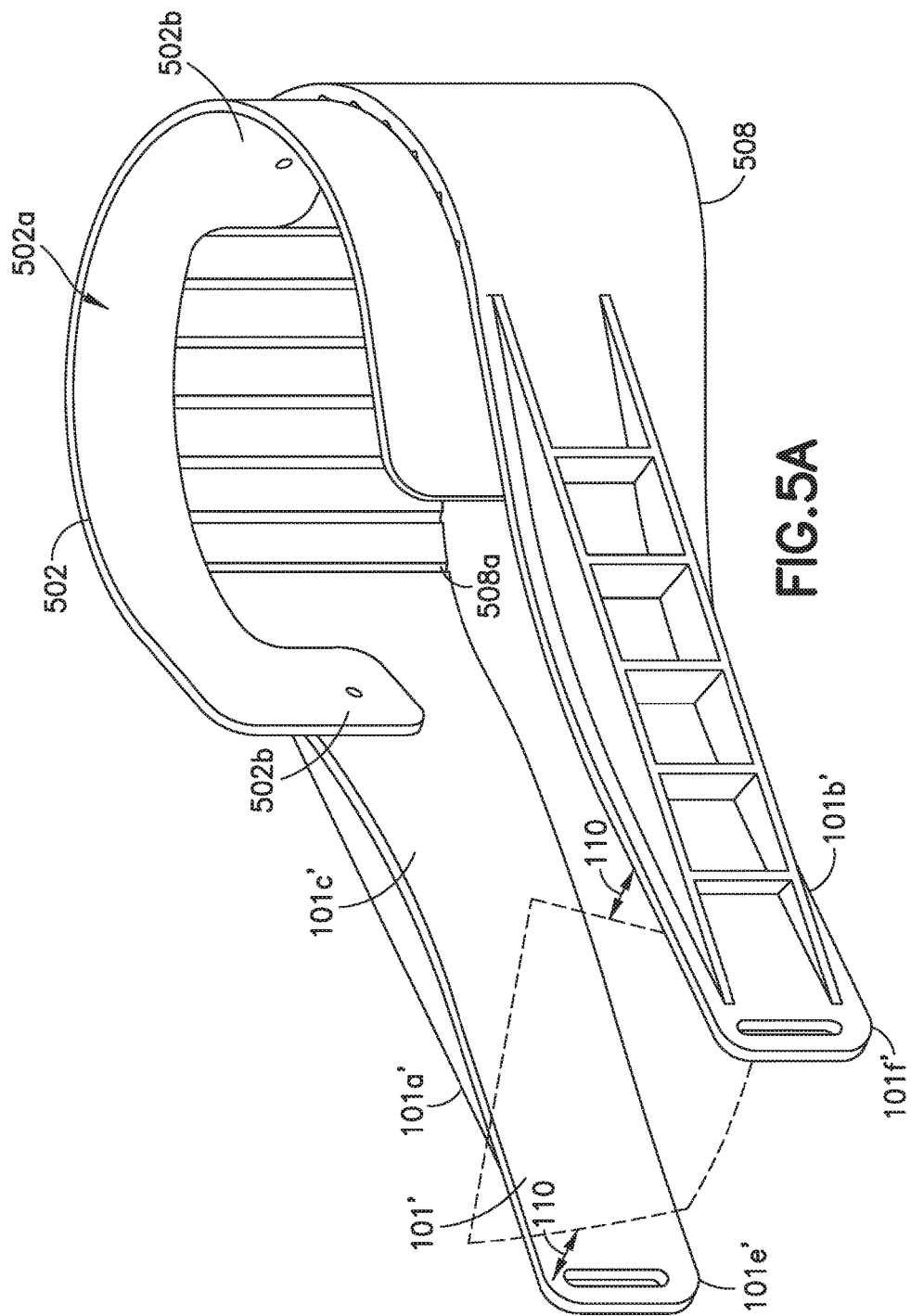

CERVICAL TRACTION COLLAR

CROSS REFERENCE TO RELATED APPLICATIONS

This application is a nonprovisional of and claims the benefit of U.S. Provisional Patent Application No. 61/897,282 filed Oct. 30, 2013, the disclosure of which is incorporated by reference herein in its entirety.

BACKGROUND

1. Field

The present embodiment relates to a cervical traction collar, more particularly, to a cervical traction collar that exerts cervical traction pressure to the base of the skull without exerting pressure on the temporomandibular joint, the jaw and/or the chin.

2. Brief Description of Related Developments

Cervical spine traction has proven to be a valuable therapeutic tool for the treatment of many cervical spine conditions such as, for example, discogenic and spondylogenic neck and arm pain. The method has also been successfully employed to help treat muscle spasms, relieve pressure on nerves and help the alignment of cervical neck bones. Because of the effectiveness of cervical spine traction as a convalescent technique, many conventional cervical traction devices have been developed and employed over the years. However, despite the wide use of such conventional cervical traction devices, these devices have several disadvantages that limit or diminish their therapeutic effect.

One disadvantage is that conventional cervical spine traction devices often limit the mobility of their users. Many cervical spine traction devices require the user to lie down, thus prohibiting the user from working or being ambulatory. Considering that the cervical spine conditions most therapeutically affected by cervical traction are also those most adversely affected by sitting, an effective cervical spine traction device that can be used in a sitting position is the most logical choice. Further, many cervical spine traction devices that require a user to lie down also tend to be highly expensive. Several conventional mobile cervical traction collars have been developed with the intention of increasing patient mobility and decreasing cost. However, these conventional mobile cervical traction devices present their own disadvantages. Conventional mobile cervical traction devices generate considerable pressure on the jaw, chin and temporomandibular joint of the patient. The literature and evolution of clinical protocols indicates that sustained pressure to the jaw, chin and temporomandibular joint increases the likelihood of injury to the temporomandibular joint. In addition to increasing the risk of injury to the patient, conventional mobile cervical spine traction devices are impractical for use for many work applications such as using a computer or sitting at a desk due to the upward pressure on the jaw and/or chin limiting user's field of view. Due to the limitations discussed above, conventional cervical traction devices are not the best solutions for providing cervical spinal traction.

BRIEF DESCRIPTION OF THE DRAWINGS

The foregoing aspects and other features of the present invention are explained in the following description, taken in connection with the accompanying drawings, wherein:

FIG. 4B is a side elevation view of the cervical traction collar as worn by a user in accordance with aspects of the disclosed embodiment.

FIG. 5 is a perspective view of a cervical traction collar in accordance with aspects of the disclosed embodiment.

FIG. 5A is a perspective view of a cervical traction collar in accordance with aspects of the disclosed embodiment.

DETAILED DESCRIPTION OF THE EXEMPLARY EMBODIMENTS

Figure 1:
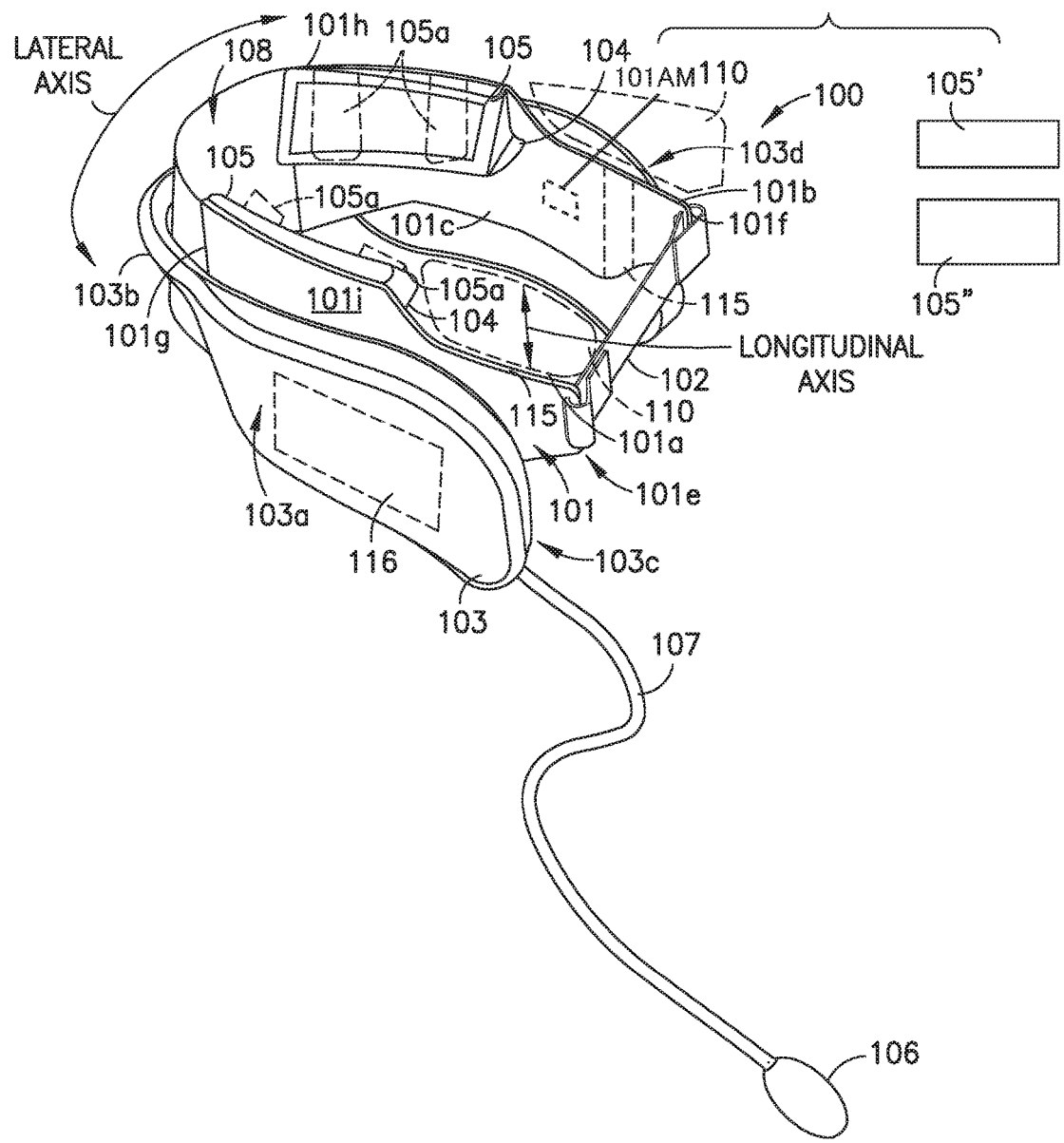
FIG. 1 is a perspective view of a cervical traction collar in accordance with aspects of the disclosed embodiment.
Figure 2:
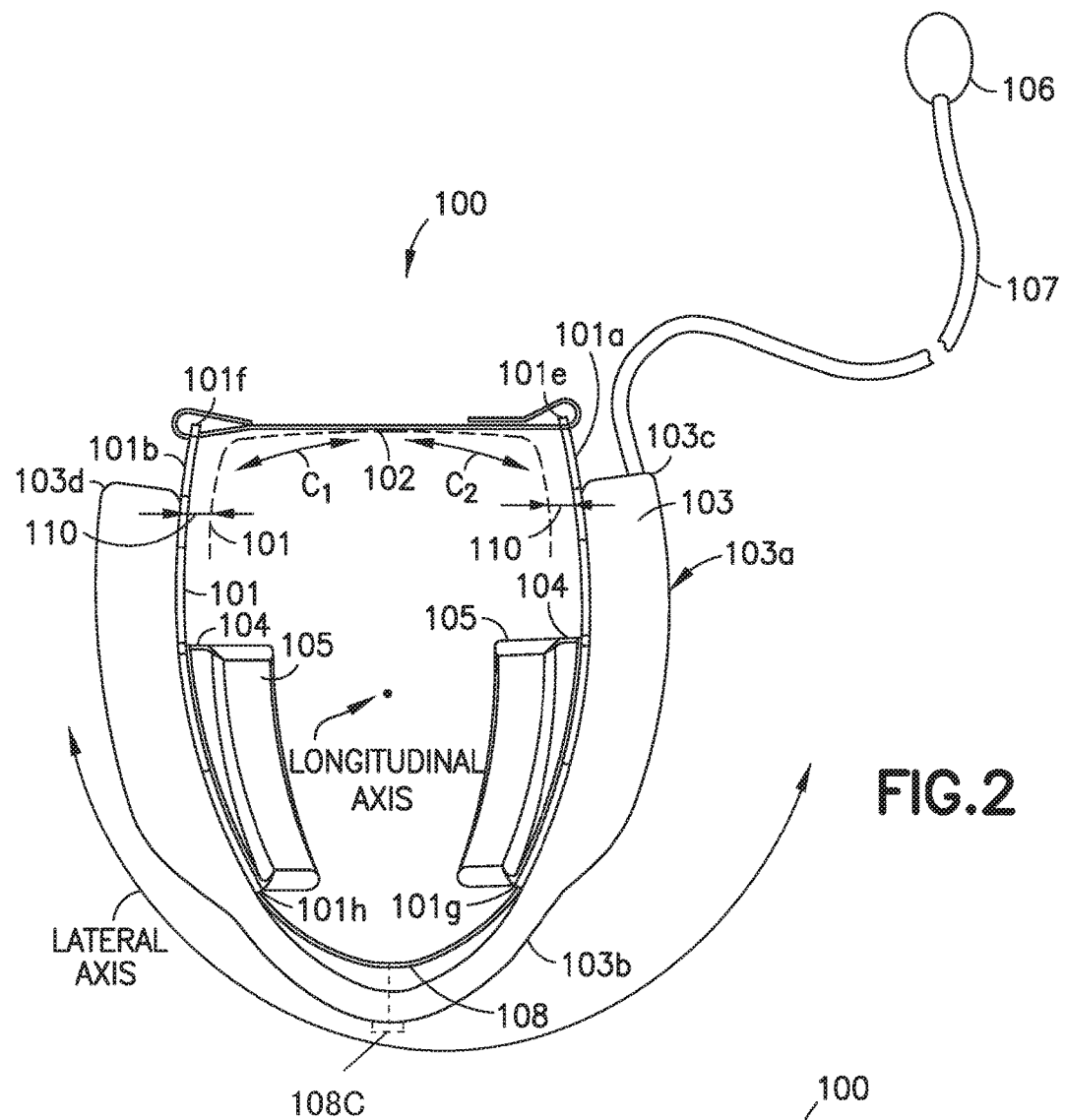
FIG. 2 is a top-down view of the cervical traction collar in accordance with aspects of the disclosed embodiment.
Figure 2A:
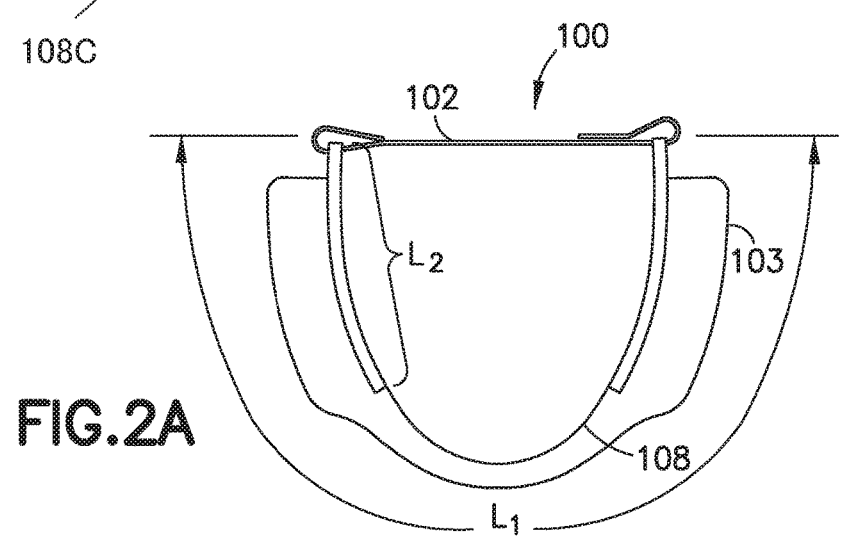
FIG. 2A is a top-down view of the cervical traction collar in accordance with aspects of the disclosed embodiment.

Referring now to FIGS. 1-2, a cervical collar 100 according to an aspect of the present disclosure is shown. The cervical collar 100 is a traction collar worn around the neck of a patient or wearer undergoing cervical spinal traction. The cervical collar 100 conforms substantially to the shape of the back of the wearer's neck and engages the shoulders of the wearer as well as the base of the wearer's skull at the occipital and/or mastoid region. The cervical collar 100 provides cervical traction pressure to the base of the skull at the occipital and/or mastoid regions without providing cervical traction pressure to the temporomandibular joint, jaw or chin of the wearer's skull. The cervical collar 100 provides the temporomandibular joint, jaw and/or chin with unobstructed clearance to enable unhindered movement. As illustrated in FIG. 1, the cervical collar 100 has a lateral axis that substantially runs along a length L1 of the cervical collar 100 (see FIG. 2A) as well as a longitudinal axis which runs transversely to the lateral axis through the cervical collar 100 (e.g. in a direction generally extending from the portion of the cervical collar 100 abutting the shoulders to the portion of the cervical collar 100 abutting the base of the skull, for example, along the direction of the wearer's neck). The cervical collar 100 can be worn by the user in any position, including lying down, standing or sitting positions.

In one aspect, the cervical collar 100 includes a semi-rigid collar portion 101, an occipital locking mechanism 104 and a traction mechanism 103, which will be discussed in further detail below. In other aspects, the cervical collar 100 has any suitable number of elements having any suitable configuration.

The semi-rigid collar portion 101 of the cervical collar 100 generally defines the shape and form of the cervical collar 100 as well as the occipital locking mechanism 104, or at least a portion thereof. The semi-rigid collar portion 101 includes semi-rigid side portions 101a, 101b, a substantially pliant or articulated joint or coupling 108 which connects the two side portions 101a, 101b (which will be described in further detail below), as well as a closure 102. The side portions 101a, 101b are substantially rigid and a portion thereof abut the sides of a wearer's neck and the base of the skull. In one aspect of the disclosed embodiment, the side portions 101a, 101b are made from a substantially rigid or semi-rigid, or generally non-pliant plastic. However, in other aspects, the side portions 101a, 101b are made from, for example, resin, fiberglass, metal, composites or any suitable substantially rigid material. The side portions 101a, 101b, though flexible in a direction transverse to the web of the respective portion, are configured to resist bending or flexing in a direction along the web, defining the semi-rigidity of the side portions 101a, 101b. The side portions 101a, 101b have joints 101g and 101h which are connected the substantially pliant joint 108 in any suitable manner, such as those described below. The side portions 101a, 101b also have free ends 101e, 101f which define a gap 110, which will be discussed in further detail below.

As noted above, the substantially pliant joint 108 connects the side portions 101a, 101b at the joints 101g and 101h, respectively, so as to form a unitary collar. In one aspect, the substantially pliant joint 108 is substantially flexible, capable of articulation that enables the semi-rigid side portions 101a, 101b to move relatively freely with respect to each other and hence substantially independently engage with the occipital and/or mastoid regions of the skull (as will be described further below). The substantially pliant joint 108 connects the side portions 101a, 101b so that the side portions 101a, 101b are able to move substantially independently relative to each other. In one aspect of the disclosed embodiment, the substantially pliant joint 108, defines, at least in part, an anti-slip portion which may or may not engage the back of the neck. However, in other aspects of the disclosed embodiment, the substantially pliant joint 108 is any joint pliant, or substantially nonresistant or less resistant to relative movement across the joint so that the adjoining semi-rigid portions 101a, 101 bare substantially independent in engagement to the base of the skull and the shoulders. The substantially pliant joint 108 is constructed from any substantially pliant material that can deform, in at least one direction without transferring torque, bending or shear loads across the joint during anticipated motion of the semi-rigid portions 101a, 101b during engagement of the occipital locking mechanism 104 against the base of the skull. In one aspect of the disclosed embodiment, the substantially pliant joint 108 is made from cloth or from any other pliant woven material. However, in other aspects, the substantially pliant joint 108 is made from a web or mesh material (for example, a plastic mesh), a flexible membrane, vinyl sheets, soft plastic sheets, thermoplastic sheets, polyethylene film or any other suitable form of compliant, deformable material which provides substantially no transfer of stresses or loads and motions (in both lateral and longitudinal axes) between the side portions 101a, 101b so that the side portions 101a, 101b effect substantially independent engagement of the occipital locking mechanism 104 to the base of the skull as will be further described. The flexibility of the substantially pliant joint 108 reduces induced displacement (e.g. sliding) of the semi-rigid portions 101a, 101b, such as in a direction tending to increase a gap between the semi-rigid collar 101 and the back of the neck (this is in comparison to conventional collars with a substantially constant stiffness across the back of the neck with resultant induced displacement bowing outwards as the side portions 101a, 101b are moved by the traction mechanism 103 to occipital locking mechanism 104 engagement). In other aspects, the substantially plaint joint reduces the likelihood of the semi-rigid collar portion 101 sliding backwards during the actuation of the traction mechanism 103. The substantially pliant joint 108 enables the semi-rigid collar portion 101 to be substantially flexible in predetermined directions or along certain predetermined axes (e.g. along the lateral axis), while also having other portions that are substantially rigid along other different predetermined directions and axes (e.g. along the longitudinal axis). In other aspects, the substantially pliant joint 108 may be formed from the substantially the same material as the side portions 101a, 101b, but thinner and more pliant. In yet other aspects, there is no substantially pliant joint 108. The semi-rigid collar 101 is, in this aspect, formed from a single piece of pre-formed rigid material having a predetermined shape and anti-slip or resistance to sliding back is effected by the configuration of the occipital locking mechanism 104 as described further below.

Figure 3:
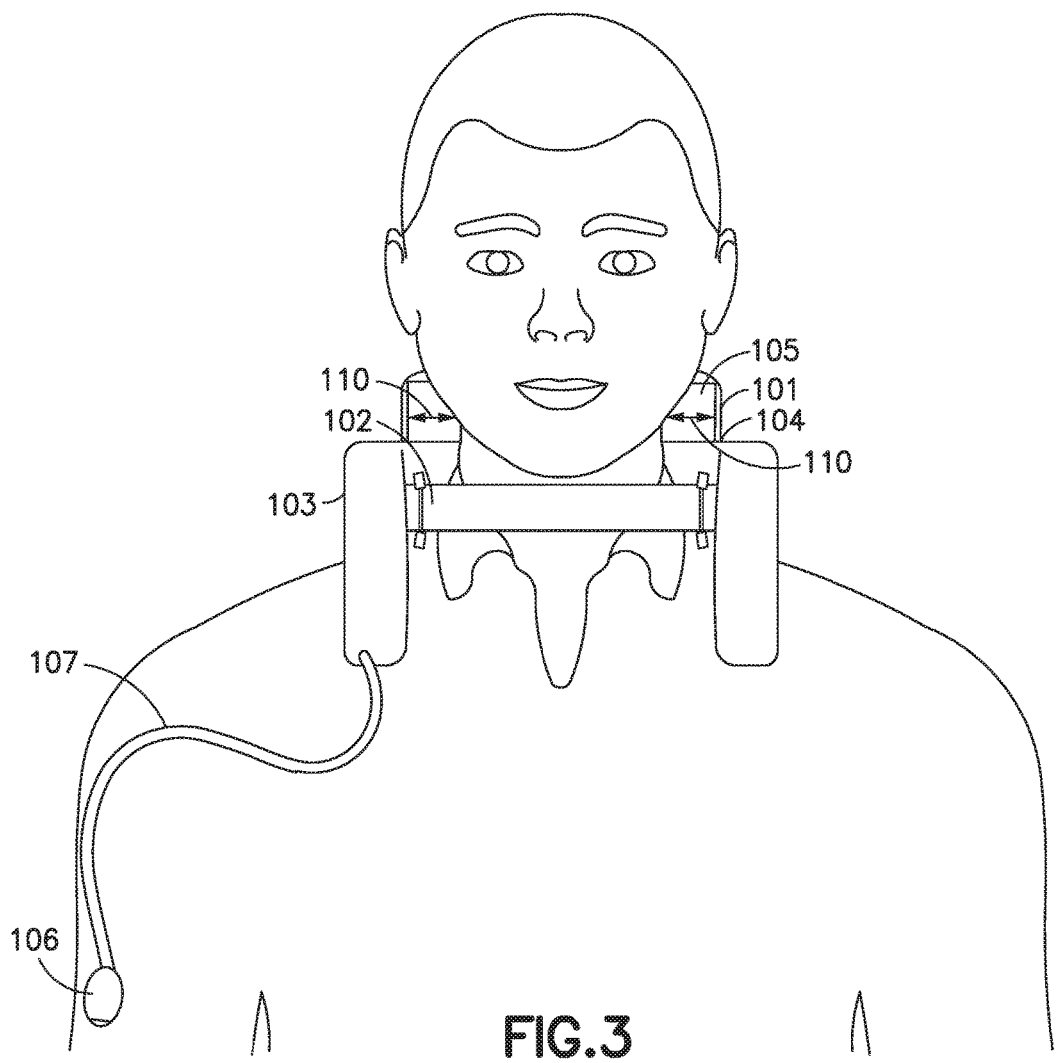
FIG. 3 is a frontal elevation view of the cervical traction collar as worn by a user in accordance with aspects of the disclosed embodiment.

Referring still to FIGS. 1-3, in one aspect, the side portions 101a, 101b are connected to the substantially pliant joint 108 by stitching. However, in other aspects, the side portions 101a, 101b are connected to the substantially pliant joint 108 by welding, mechanical connectors (such as clips and/or snaps), ties, laces, chemical bonding or any suitable form of connection. The semi-rigid collar portion 101 is also flexible to enable or facilitate the opening and closing of the cervical collar 100 in, for example, the direction of arrows C1, C2 as shown in FIG. 2. For example, the substantially pliant joint 108 enables the semi-rigid collar portion 101 to be readily opened so that it is substantially flat. The flexibility of the substantially pliant joint 108 enables the semi-rigid side portions 101a, 101b of the semi-rigid collar portion 101 to substantially independently engage the base of the skull at the occipital and/or mastoid region as cervical traction pressure is applied to the base of the skull at the occipital and/or mastoid regions. In one aspect, the length of the semi-rigid collar portion 101 (which, in one aspect, is substantially the same as length L1) is adjustable. For example, the semi-rigid collar portion 101 has ratcheting mechanisms 115 (FIG. 1 built into the side portions 101a, 101b. The ratcheting mechanisms enable the user to adjust a length L2 (see FIG. 2A) of the side portions 101a, 101b to accommodate users and wearers of different sizes and shapes. In other aspects, the length of the semi-rigid collar portion 101 can be adjusted by any suitable form of mechanism, including, for example, snaps or clips coupled to the substantially pliant joint 108 to adjust the length of the substantially pliant joint 108. In yet other aspects, the height of the semi-rigid collar portion 101 can be adjusted as well to accommodate wearers and users of different sizes and shapes. For instance, in one aspect, the side portions 101a, 101b may have adjustable ratcheting mechanisms or any other suitable adjustment mechanisms (not shown) which increase the height of the rigid collar portion. In other aspects, an additional height spacer may be added to adjust or enhance the height of the semi-rigid collar portion 101. In yet other aspects, height adjustment of the semi-rigid collar 101 employs any suitable height adjustment method.

Figure 4A:
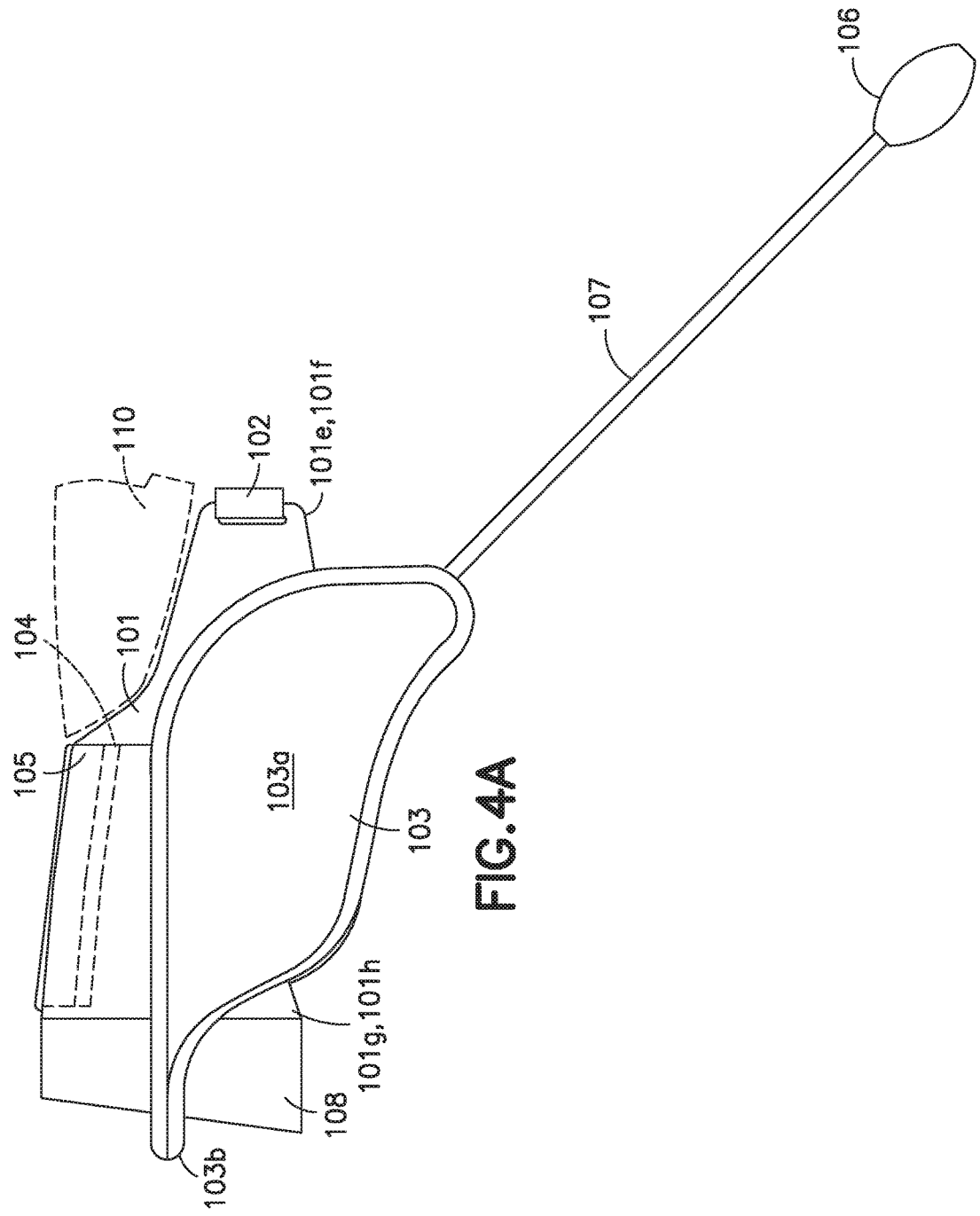
FIG. 4A is a side elevation view of the cervical traction collar in accordance with aspects of the disclosed embodiment.

As can be seen in FIGS. 1, 2, 3, 4A and 4B, the semi-rigid collar portion 101 has a gap 110 located in the front (e.g. relative to the wearer or user) of the cervical collar 100. The gap 110 substantially corresponds to the front of the neck and throat of a wearer and provides a region of substantially unobstructed clearance for the jaw, chin and temporomandibular joint of the skull to prevent engagement or application of pressure to these regions. In one aspect, the gap 110 is a substantially longitudinal (e.g. vertical) gap and is defined by a detente portion or a recessed and/or tapered portion of the free ends 101e, 101f as seen in FIGS. 1, 4A and 4B. The gap 110 as shown in FIGS. 1, 4A and 4B provides unhindered clearance for the wearer's jaw, chin and/or temporomandibular joint to enable the unencumbered movement of the jaw and/or chin, thus allowing a wearer to talk, chew, or tilt their head up and down. The gap 110 provides a region of unobstructed clearance for the jaw, chin and temporomandibular joint of the skull to prevent engagement or application of pressure to these regions. The gap 110 is further enhanced by tapering or thinning (along the web) the side portions 101a and 101b at the free ends 101e, 101f. The tapered or thinned free ends 101e, 101f helps define a recessed portion to augment the unobstructed clearance for the jaw, chin and temporomandibular joint. As shown in FIGS. 1, 4A and 4B, the gap 110 corresponds to the recessed or tapered portions of the free ends 101e, 101f that accommodate the wearer's jaw, chin and/or temporomandibular joint (shown in phantom). In other aspects, the gap 110 may also include a substantially lateral gap component comprising of a gap which spans the regions between the free ends 101e, 101f and the wearer's jaw, chin and/or temporomandibular joint. As seen in FIGS. 2 and 3, in one aspect, a lateral gap component of the gap 110 may also be provided that corresponds to the space between the free ends 101e, 101f and the user's jaw, chin and/or temporomandibular joint (shown in phantom in FIG. 2). However, in other aspects, there is no lateral gap, for example, where the free ends 101e, 101f are connected and joined under a wearer's jaw or chin and there is no or substantially no lateral space between the wearer's jaw, chin and temporomandibular joint and the free ends 101e, 101f. In yet other aspects, the gap 110 includes any suitable combination of longitudinal or lateral gap components which provides for unencumbered clearance for the wearer's jaw, chin and/or temporomandibular joint. In yet other aspects, the lateral gap component of gap 110 is formed from the shape of side portions 101a, 101b, for instance, when the side portions 101a, 101b is angled away (for instance, in an outward and/or downward direction, or in other aspects, a downward and/or inward direction) from the side of the temporomandibular joint, jaw and/or chin to create an unobstructed clearance for the temporomandibular joint, jaw and/or chin.

In one aspect, the semi-rigid collar portion 101 has a closure 102 which connects the free ends 101e, 101f of the side portions 101a, 101b. The closure 102 provides adequate room to comfortably accommodate the front of the neck and throat. The gap 110 facilitates closing the cervical collar 100 opening fully without discomfort to the wearer's neck and throat. In one aspect, the closure 102 may be left open, or there may be no closure 102. The occipital locking mechanism 104 can remain fully engaged without support as described. In one aspect of the disclosed embodiment, the closure 102 is a strap. However, in other aspects, the closure 102 is any suitable form of closure which spans and connects the free ends 101e, 101f of the side portions 101a, 101b such as, for example, clasps, latches, hook and loop fastener straps, straps with buckles or straps with snaps. In one aspect, the closure 102 is a substantially pliant member, for example, made of pliable straps, laces, cords or any other suitable pliant material. However, in other aspects, the closure 102 is substantially rigid and is made from plastic, composite, metal or any other suitable rigid material. In one aspect, the closure 102 is connected to the free ends 101e, 101f by any suitable connection, including a hinge, looping through an aperture at the free ends 101e, 101f, hook and loop fasteners and/or an adhesive. In yet other aspects, the closure 102 is omitted so that the semi-rigid collar portion 101 is in an open position with the free ends 101e, 101f being unfastened. In this aspect, the semi-rigid collar portion 101 includes suitable structure (such as pliable, resilient or rigid support members) that connect the side portions 101a, 101b through the substantially pliant joint 108 so that the semi-rigid collar portion 101, and more specifically, the occipital locking mechanism 104 thereof, remains fully and reliably engaged during the actuation of the traction mechanism 103. In one aspect of the disclosed embodiment, the closure 102 is located at the back of the semi-rigid collar portion 101.

In one aspect of the disclosed embodiment, the semi-rigid collar portion 101 also has an occipital locking mechanism 104 or forms the occipital locking mechanism 104 or part thereof. The occipital locking mechanism 104 is connected or mounted on, or otherwise formed on, an interior surface 101c or other suitably oriented portion of the semi-rigid side portions 101a, 101b. Such suitable portions of the side portions 101a, 101b face and substantially engage the base of the skull. The occipital locking mechanism 104 includes any part of the semi-rigid collar 101 (for example, the side portions 101a, 101b) that is configured to abut and engage with the base of the skull at the occipital and/or mastoid region of the skull to provide cervical traction pressure without engaging or touching the temporomandibular joint, jaw or chin. The occipital locking mechanism 104 forms a protrusion relative to the adjoining gapped portion of the semi-rigid collar portion 101 which, under the impetus from the traction mechanism 103 action on the side portions 101a, 101b, provides for an enhanced clamping effect on the occipital and/or mastoid region of the skull by the side portions 101a, 101b while allowing for additional clearance for the jaw, chin and/or temporomandibular joint, as well as the side of the neck and throat by the side portions 101a, 101b. The occipital locking mechanism 104 enables the application of cervical traction pressure generated by the traction mechanism 103 (to be discussed in greater detail below) directly to the occipital and/or mastoid region of the skull. In one aspect of the disclosed embodiment, the occipital locking mechanism 104 is formed from parts of (or is integral with) parts of the semi-rigid collar portion 101 such as the side portions 101a, 101b. In this aspect, the shape of the side portions 101a, 101b defines an occipital locking mechanism 104 which transfers cervical traction pressure from the rigid side portions 101a, 101b to the base of the skull at the occipital and/or mastoid region. In one aspect of the disclosed embodiment, the occipital locking mechanism 104 is formed from any suitable portion of the semi-rigid collar 101 which enables for the transfer of cervical traction stress to the occipital and/or mastoid region of the skull. Suitable portions include, for instance, the top edge 120 of the side portions 101a, 101b, the interior surface 101c of the side portions 101a, 101b, the exterior surface 101i of the side portions 101a, 101b, or any other suitable part of the semi-rigid collar 101 disposed facing and engaging the base of the skull as previously described. In one aspect, the occipital locking mechanism 104 is formed or directly molded into the semi-rigid collar 101 or side portions 101a, 101b. In other aspects, the occipital locking mechanism 104 includes any suitable feature mounted or coupled to parts of the semi-rigid collar 101, such as, for example, a protrusion or engagement feature mounted on or coupled to the side portions 101a, 101b. In one aspect, the occipital locking mechanism 104 is one or more protrusions extending from the interior surface 101c of the semi-rigid collar portion 101 so as to abut the base of the skull at the mastoid or occipital region. In yet other aspects, the occipital locking mechanism 104 is a protrusion mounted to the exterior surface 101i, the top edge 120 of the side portions 101a, 101b or any other suitable place. In one aspect of the disclosed embodiment, the occipital locking mechanism 104 has a substantially flat shape perpendicular to the interior surface 101c of the semi-rigid collar 101. However, in other aspects of the disclosed embodiment, the occipital locking mechanism 104 has a wedge or inclined shape to effect the transfer of cervical traction pressure against the base of the skull to prevent slippage as well as to increase comfort. In yet other aspects, the occipital locking mechanism 104 has any suitable form or shape to transfer cervical traction pressure against the base of the skull, including, for instance, a round shape. As noted, the protrusions can be mounted to the interior surface 101c, or can be integrally formed as part of the side portions 101a, 101b. However, in yet other aspects, the occipital locking mechanism 104 is a cushion or padding applied over the side of the side portions 101a, 101b to abut and engage the occipital and/or mastoid region of the skull. The occipital locking mechanism 104 allows for selective and directed application of cervical traction pressure.

In one aspect, the occipital locking mechanism 104 has contact cushions 105 coupled thereon to increase wearer comfort. The contact cushions 105 directly engage and contact the occipital and/or mastoid region of the skull. In one aspect of the disclosed embodiment, the contact cushions 105 are made from a substantially compliant and conformal material which conforms to the shape of the occipital and/or mastoid region. The substantially compliant and conformal material of the contact cushions 105 prevents injury or pain from the cervical traction pressure exerted by the occipital locking mechanism on the occipital and/or mastoid region of the skull. In one aspect of the disclosed embodiment, the contact cushion 105 is made from foam. However, in other aspects, the contact cushion 105 is made from soft latex, silicone, mesh, padding or any other suitably compressible and conformal material. In yet another aspect, the contact cushion 105 is a compressible air bladder to generate increased contact to the occipital and/or mastoid region to prevent slippage during the application of cervical traction pressure. In one aspect, the contact cushions 105 are fixed cushions. However, in other aspects, the contact cushions 105 are interchangeable with different contact cushions 105', 105", each having a different predetermined shape and size to accommodate users of different shapes and sizes. In yet other aspects, the contact cushions 105 have spacers 105a built into the contact cushions 105 to further facilitate fit and transfer of cervical traction pressure against the base of the skull at the occipital and/or mastoid regions. In another aspect of the disclosed embodiment, the contact cushions 105 are substantially wedged or inclined (see FIGS. 1 and 3) to facilitate the transfer of cervical traction pressure against the base of the skull. However, in other aspects, the contact cushions 105 are flat or round or any other suitable shape. In yet other aspects, the occipital locking mechanism 104 does not include contact cushions 105 at all.

Referring now to FIGS. 1-3, the cervical traction pressure applied by the occipital locking mechanism 104 to occipital and/or mastoid region of the skull is generated by the traction mechanism 103. In one aspect of the disclosed embodiment, the traction mechanism 103 is any mechanism which generates a cervical traction pressure or force against the occipital and/or mastoid region of the skull. It should be noted that while the traction mechanism 103 is described separately from the semi-rigid collar 101 and the occipital locking mechanism 104, this is done purely for descriptive purposes. In some aspects of the disclosed embodiment, the traction mechanism 103 includes any suitable part of the semi-rigid collar 101 and may be incorporated at least in part in the occipital locking mechanism 104 which is configured to generate a cervical traction pressure. In other aspects of the disclosed embodiment, the occipital locking mechanism 104 and semi-rigid collar 101 also may include any suitable part of the traction mechanism 103. The interface between the traction mechanism 103, the semi-rigid collar 101 and occipital locking mechanism 104 described herein is used for convenience and description purposes only and may vary as desired.

Referring again to FIGS. 1-3, in one aspect of the disclosed embodiment, the traction mechanism 103 is coupled to the semi-rigid collar portion 101 and, when actuated, generates a cervical traction pressure in the direction of arrow Y (see FIG. 4A) which is transferred through the semi-rigid collar portion 101 to the occipital locking mechanism 104. In one aspect of the disclosed embodiment, the traction mechanism 103 is coupled to the exterior surface 101i of the semi-rigid collar portion 101 (see FIGS. 1-3, 4A-4B) in any suitable manner. The exterior surface 101i of the semi-rigid collar portion 101 is the surface of the semi-rigid collar portion 101 that faces away from the neck of the wearer. In other aspects, the traction mechanism 103 is coupled to any suitable part of the semi-rigid collar portion 101 that is suitable for generating and providing cervical traction pressure. For example, in another aspect, the traction mechanism 103 is coupled to the portion of the semi-rigid collar portion 101 that abuts and engages with the shoulders of the wearer. In one aspect, the traction mechanism 103 is fixedly and permanently connected to the semi-rigid collar portion 101, such as, for example, using a rigid connector (not shown) between the semi-rigid collar portion 101 and the traction mechanism 103. In other aspects, the connection is any suitable form of connection strong enough to withstand pressures exerted during cervical traction.

In one aspect of the disclosed embodiment, the traction mechanism 103 includes an inflatable, air-impervious bladder 116 which generates cervical traction pressure when it is inflated. In this aspect, the air-impervious bladder 116 is constructed from material such as plastic, rubber, silicone, vinyl, polyethylene film, urethane or any other suitable air-impervious membrane. The inflation of air bladder 116 generates a cervical traction pressure in the direction of arrow Y (see FIG. 4A) against at least the shoulders of the wearer. The cervical traction pressure against the shoulders pushes the semi-rigid collar portion 101 along the longitudinal axis away from the shoulders, which in turn pushes the occipital locking mechanism 104 against the occipital and/or mastoid region of the skull. In other aspects of the disclosed embodiment, the traction mechanism 103 is any suitable form of actuator, including, for example, hydraulic actuators, mechanical actuators (for example, linear actuators, screws or a pulley system), electromagnetic actuators, chemical actuators or manual manipulation. In yet other aspects, the traction mechanism 103 is a mechanical tensioning or decompression system (for example, a mechanical slide table) or any other suitable mechanical actuator configured to generate a cervical traction force along a longitudinal axis which is coupled to the semi-rigid collar 101 through either frictional engagement, direct coupling or indirect coupling. In other aspects, the traction mechanism 103 includes wedges used to generate cervical traction pressure. In one aspect of the disclosed embodiment, the air bladder 116 of the traction mechanism 103 is covered by a cover material 103a such as, for example, a woven material (such as cloth or wool), a membrane, a mesh material, flocked vinyl or any other substantially pliant material. In one aspect, cover material 103a enables the attachment of an air bladder 116 (to be described in further detail below) to the semi-rigid collar 101. In other aspects, the cover material 103a increases the durability of the traction mechanism 103 to, for example, prevent accidental puncture or popping. The cover material 103a also provides for the comfort of the wearer of the cervical collar 100 by increasing the softness and/or warmth of the traction mechanism 103. In other aspects, the cover material 103a also increases the grip of the traction mechanism 103 as it engages the shoulders of the wearer. In another aspect of the disclosed embodiment, the cover material 103a effects and controls the inflation of the traction mechanism 103. For example, the cover material 103a is configured to affect the inflation of the traction mechanism 103 by having predetermined areas of the cover material 103a being constructed from a less pliant material (for example, along the side of the traction mechanism 103) to prevent loss of pressures to a side blowout (whereby pressure is lost by being exerted on the sides of the traction mechanism 103 instead of longitudinally in a direction of cervical traction). The cover material 103a controls the inflation of the traction mechanism 103 so that greater longitudinal force is generated along the longitudinal axis. In one aspect, the traction mechanism 103 also has baffles built into the inflatable air bladders of the traction mechanism 103 to further direct the flow of air and control the inflation of the traction mechanism 103. In one aspect, the baffles also prevent loss of inflation pressure to side blowouts.

In one aspect of the disclosed embodiment, the traction mechanism 103 is actuated by inflating the air-impervious bladder 116 of the traction mechanism 103. In this aspect, inflation is effected with the hand-actuated bulb pump 106 and a pneumatic tube 107, which connects the bulb pump 106 to the traction mechanism 103. In other aspects, the traction mechanism 103 is actuated in any suitable manner, including with a mechanical air pump, hydraulics, mechanical actuators, electromagnetic actuators or chemical actuators. In one aspect of the disclosed embodiment, the bulb pump 106 has a pressure relief valve to limit the cervical traction pressure generated by the bulb pump 106. In other aspects, the pressure relief valve is located in any suitable part of the traction mechanism 103, including, for instance, the air bladder 116. In yet other aspects, there may be more than one independent actuator for the traction mechanism 103. For example, there may be multiple independent pumps coupled to either side of the traction mechanism 103. In other aspects, actuation of the traction mechanism 103 can have any suitable configuration. The cervical traction pressure is transferred from the traction mechanism 103 to the occipital locking mechanism 104 through the side portions 101a, 101b of the semi-rigid collar portion 101. The occipital locking mechanism 104, in turn, applies the transferred cervical traction pressure along the longitudinal axis to the occipital and/or mastoid regions of the skull without applying cervical traction pressure to the jaw, chin and temporomandibular joint.

In one aspect of the disclosed embodiment, the traction mechanism 103 has a predetermined shape to maximize cervical traction pressure generated by the traction mechanism 103. Referring to FIGS. 3 and 4B, the traction mechanism 103 is substantially concaved where the traction mechanism abuts the shoulders of the user (e.g. conforms to a shape of the user's shoulders). The substantially concaved shape of the traction mechanism allows for better grip and stability of the traction mechanism 103 on the shoulders to maximize generation of cervical traction pressure. In another aspect (see FIG. 1-2), the traction mechanism 103 has a two-lobe configuration with lobes 103c, 103d where, in one aspect, each lobe 103c, 103d includes a respective air bladder 116 communicably coupled to each other to allow gas passage between the air bladders. The lobes 103c, 103d ensure that maximum inflation pressure is directed against the shoulders. In one aspect of the disclosed embodiment, the split traction mechanism configuration of lobes 103c, 103d preserves the flexibility and pliancy of the substantially pliable joint 108. The two lobes 103c, 103d are fluidically coupled by tube portion 103b. The tube portion 103b enables the communication of fluid (e.g. gas) from one lobe 103c to the other lobe 103d. In one aspect, the tube portion 103b is made from a more rigid or less pliant material than the air bladders of the traction mechanism 103. In other aspects, the tube portion 103b is made from the same material as the air bladders 116, but substantially thicker and less pliant. The tube portion 103b minimizes lost pressure used to inflate the portion of the traction mechanism 103 along the back of the neck (e.g. due to expansion of the tube portion 103b) and maximizes longitudinal cervical traction pressure generated against the shoulders by the traction mechanism 103 in the direction of arrow Y.

Referring now to FIGS. 5 and 5A, another aspect of a semi-rigid collar portion is shown. The features of the semi-rigid collar portion 101' shown in FIG. 5 substantially correspond to the features of the semi-rigid collar portion 101 shown in FIG. 1-2. The semi-rigid collar portion 101' has side portions 101a', 101b' which corresponds to the side portions 10a, 101b. The side portions 101a', 101b' are substantially long and rigid portions which substantially extend along the side of the wearer's neck. In one aspect of the disclosed embodiment, the side portions 101a' and 101b' are made from a rigid plastic. However, in other aspects, the side portions 101a' and 101b' are made from, for example, resin, fiberglass, metal, composite or any suitable substantially rigid material. The side portions 101a' and 101b' are configured to resist bending or flexing, either from longitudinal pressure along the longitudinal axis or lateral pressure along the lateral axis. In one aspect of the disclosed embodiment, the side portions 101a', 101b' are reinforced by rib members 501. The rib members 501 are of a unitary construction with the side portions 101a', 101b'. The rib members 501 substantially increases the rigidity of the side portions 101a', 10b' and increases their resistance to flexing or bending during application of cervical traction pressure.

In one aspect of the disclosed embodiment, the side portions 101a', 101b' are joined together by an articulated joint or hinge member 508. The articulated joint or hinge member 508 is any suitable joint with release for relative movement, for example, torsional movement, sliding movement or bending movement through pin and groove joints or ball socket joints. In one aspect, the hinge member 508 is formed of a single piece of material such as rigid plastic. However, in other aspects, the hinge member 508 is made from, for example, resin, fiberglass, metal, composite or any suitable substantially rigid material. In yet other aspects, the hinge member 508 is made from discrete links individually connected to each other similar to the links of a metal watch band. In one aspect, the hinge member 508 is of unitary construction with the rigid side members 101a', 101b'. However, in other aspects, the hinge member 508 is a separate and distinct hinge member which is joined to the side portions 101a', 101b' in any suitable manner such as by mechanical connectors, welding, stitching, chemical bonding or any suitable connection. The hinge member 508 has cutouts or grooves 508a cut into the surface of the hinge member 508. The grooves 508a thin the cross-section of the hinge member 508 in predetermined areas to permit the hinge member 508 to flex and bend along the lateral axis, for example, along arrows C1', C2'. The lateral flexibility of the hinge member 508 enables the semi-rigid collar portion to open and close to accommodate the neck of a wearer in a way substantially similar to the semi-rigid collar portion 101 and the substantially pliant joint 108. However, because of the orientation of the grooves 508*a* and the rigid construction material of the hinge member 508, the hinge member 508 is flexible along the lateral axis and is substantially rigid and resilient to pressure along the longitudinal axis. The side portions 101*a*' and 101*b*' have ends 101*e*' and 101*f*' which define a gap 110' substantially similar to gap 110. However, in other aspects, the semi-rigid collar 101' is pre-curved and formed substantially of a single piece of material and does not have a hinge member 508.

Referring still to FIGS. 5 and 5A, the semi-rigid collar portion 101' is adjustable for different heights. The height adjustment attachment 502 is a collar attachment which is movably coupled to the interior surface 101*c*' of the semi-rigid collar portion 101'. The height adjustment collar 502 is adjustable in height relative to the semi-rigid collar portion 101' to accommodate users of different sizes and shapes. Though not shown in FIG. 5, in one aspect, an occipital locking mechanism similar to the occipital locking mechanism 104 and contact cushion 105 shown in FIGS. 1-2 is attached to the interior surface 502*a* of the height adjustment attachment 502. By adjusting the height adjustment attachment 502, the wearer or user is allowed to fine-tune the degree of engagement or cervical traction force directed to the base of the skull at the occipital and/or mastoid regions by the occipital locking mechanism. In one aspect, the height adjustment attachment 502 is made from a semi-rigid material, such as, for example plastic or resin. However, in other aspects, the height adjustment attachment 502 is made from any suitable material which is rigid along the longitudinal axis (to enable the transfer of cervical traction pressure) and flexible along the transverse axis (to enable flexing for opening and closing the semi-rigid collar portion 101'). As can be seen in FIG. 5A, the height adjustment attachment 502 is substantially flush against the interior surface 101*c*' of the semi-rigid collar portion 101' when coupled to the semi-rigid collar portion 101'.

Figure 6:
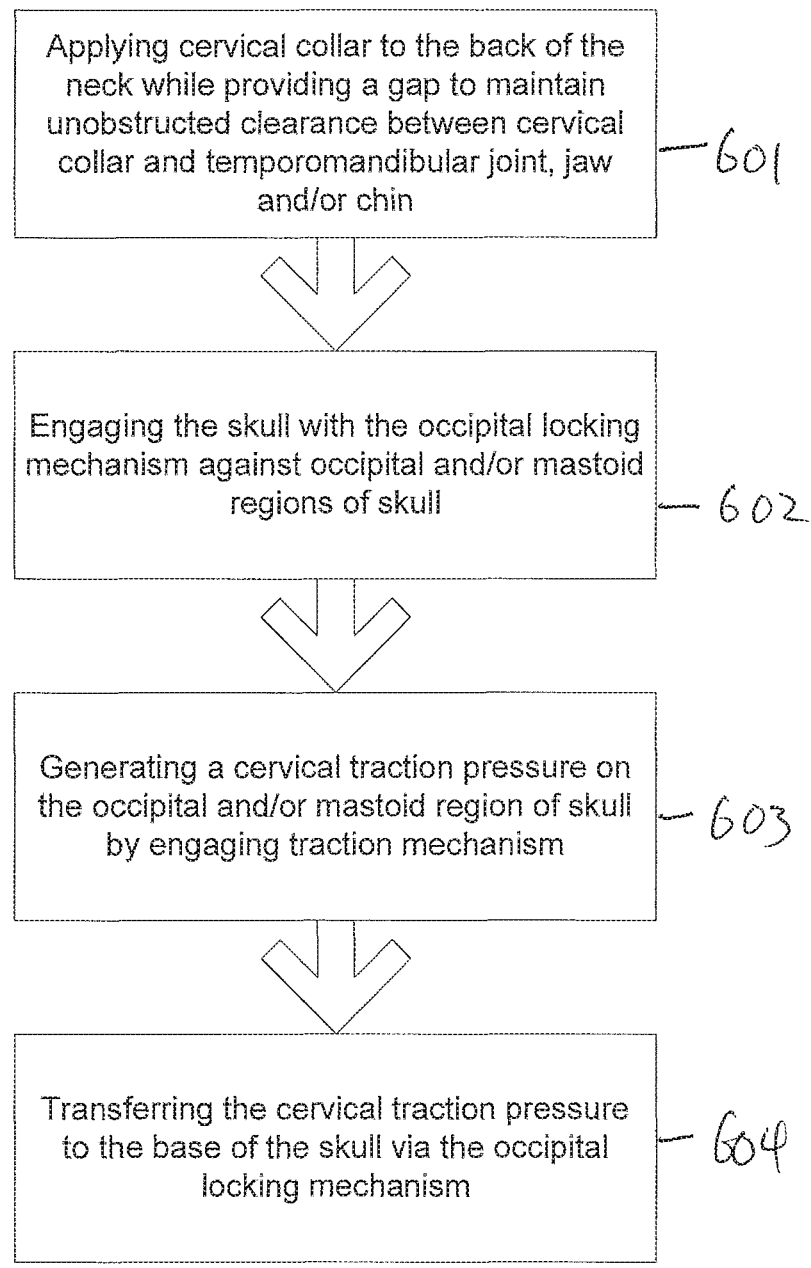
FIG. 6 is an exemplary flow chart illustrating the operation of the cervical traction collar in accordance with aspects of the disclosed embodiment.

Referring now to FIG. 6, an exemplary flow chart illustrating the operation of the cervical collar 100 is presented. At block 601, the cervical collar 100 is applied to the neck. The cervical collar 100 is provided with a gap 110 to maintain an unobstructed clearance between the cervical collar 100 and the temporomandibular joint, jaw and/or chin of the skull. At block 602, the skull is engaged with the occipital locking mechanism 104 of the cervical collar 100 against occipital and/or mastoid regions of the skull. At block 603, a cervical traction pressure is generated on the occipital and/or mastoid region of the skull by engaging and actuating a traction mechanism 103 of the cervical collar 100. The gap 110 is maintained in the cervical collar 100 during the actuation of the traction mechanism 103 to maintain a continued unobstructed clearance between the cervical collar 100 and the temporomandibular joint, jaw and chin. At block 604, the cervical traction pressure is transferred to the base of the skull at the mastoid or occipital regions via the occipital locking mechanism 104.

In accordance with one or more aspects of the disclosed embodiment, a cervical collar includes a semi-rigid collar substantially conforming to the back of a neck, an occipital locking mechanism coupled to the semi-rigid collar, configured to generally conform to and engage with the base of a skull at the occipital or mastoid region without engaging the temporomandibular joint, jaw or chin of the skull, a traction mechanism coupled to the semi-rigid collar, the at least one traction mechanism configured to provide cervical traction through the occipital locking mechanism of the semi-rigid collar against the base of the skull without pressure against the temporomandibular joint, jaw or chin.

In accordance with one or more aspects of the disclosed embodiment, the semi-rigid collar has a gap which maintains an unobstructed clearance between the cervical collar and the temporomandibular joint, jaw and chin with the traction mechanism engaged to provide cervical traction.

In accordance with one or more aspects of the disclosed embodiment, the cervical collar further includes a fastening system connected to the semi-rigid collar.

In accordance with one or more aspects of the disclosed embodiment, the traction mechanism further comprises at least one inflatable bladder.

In accordance with one or more aspects of the disclosed embodiment, the traction mechanism has a common inflation mechanism.

In accordance with one or more aspects of the disclosed embodiment, the traction mechanism has multiple inflation mechanisms.

In accordance with one or more aspects of the disclosed embodiment, the traction mechanism is configured to engage the shoulders at a base of the semi-rigid collar.

In accordance with one or more aspects of the disclosed embodiment, the at least one inflatable bladder has at least one baffle configured to control inflation of the at least one inflatable bladder.

In accordance with one or more aspects of the disclosed embodiment, the semi-rigid collar further includes a substantially flexible anti-slip portion having a pliant, non-resilient coupling.

In accordance with one or more aspects of the disclosed embodiment, wherein the pliant coupling couples semi-rigid portions of the semi-rigid collar so that the coupled semi-rigid portions are substantially independent portions relative to each other configured for substantially independent engagement with the occipital locking mechanism.

In accordance with one or more aspects of the disclosed embodiment, the semi-rigid collar is substantially reinforced at least one rib structure.

In accordance with one or more aspects of the disclosed embodiment, the occipital locking mechanism is configured to provide cervical traction pressure to the occipital or mastoid region of the skull without pressure to the temporomandibular joint, jaw or chin.

In accordance with one or more aspects of the disclosed embodiment, the traction mechanism is at least one inflatable bladder.

In accordance with one or more aspects of the disclosed embodiment, the at least one inflatable bladder is coupled to an exterior or interior surface of the semi-rigid collar.

In accordance with one or more aspects of the disclosed embodiment, the at least one traction mechanism has a common inflation mechanism.

In accordance with one or more aspects of the disclosed embodiment, the traction mechanism has multiple inflation mechanisms.

In accordance with one or more aspects of the disclosed embodiment, the at least one traction mechanism is configured to engage the shoulders at the base of the semi-rigid collar.

In accordance with one or more aspects of the disclosed embodiment, the at least one traction mechanism is configured to generate the cervical traction pressure along a longitudinal axis.

In accordance with one or more aspects of the disclosed embodiment, the at least one traction mechanism has at least two lobes in fluid communication with each other.

In accordance with one or more aspects of the disclosed embodiment, the at least one traction mechanism engage the shoulders to generate the cervical traction pressure while using the shoulders as a fulcrum for the semi-rigid collar.

In accordance with one or more aspects of the disclosed embodiment, the semi-rigid collar has a substantially split configuration, comprising of two substantially rigid side portions defining a respective left and right side portions of the occipital locking mechanism joined by a pliant joint decoupling the left and right side portions of the occipital locking mechanism so that the respective occipital locking mechanism portions are substantially independent in engagement to the base of the skull.

In accordance with one or more aspects of the disclosed embodiment, the at least one traction mechanism is a mechanical pulley system.

In accordance with one or more aspects of the disclosed embodiment, the at least one traction mechanism is a mechanical tensioning system.

In accordance with one or more aspects of the disclosed embodiment, the mechanical tensioning system is frictionally engaged with the semi-rigid collar.

In accordance with one or more aspects of the disclosed embodiment, the mechanical tensioning system is coupled to the semi-rigid collar.

In accordance with one or more aspects of the disclosed embodiment, the at least one traction mechanism is manually actuated.

In accordance with one or more aspects of the disclosed embodiment, a cervical collar includes a semi-rigid collar having an interior surface; the semi-rigid collar further having a gap which maintains an unobstructed clearance between the cervical collar and the temporomandibular joint, jaw and chin of a skull, an occipital locking mechanism on the semi-rigid collar, configured to generally conform to and engage with the base of the skull at the occipital or mastoid region, a traction mechanism coupled to the semi-rigid collar, the traction mechanism configured to provide cervical traction through the occipital locking mechanism of the semi-rigid collar against the base of the skull. The gap of the semi-rigid collar persists when the traction mechanism is engaged to provide cervical traction.

In accordance with one or more aspects of the disclosed embodiment, the cervical collar further includes a fastening system connected to the semi-rigid collar and spanning the gap of the semi-rigid collar while maintaining the gap.

In accordance with one or more aspects of the disclosed embodiment, the traction mechanism further comprises at least one inflatable bladder.

In accordance with one or more aspects of the disclosed embodiment, the traction mechanism has a common inflation mechanism.

In accordance with one or more aspects of the disclosed embodiment, the traction mechanism has multiple inflation mechanisms.

In accordance with one or more aspects of the disclosed embodiment, the at least one inflatable bladder has at least one baffle configured to control inflation of the at least one inflatable bladder.

In accordance with one or more aspects of the disclosed embodiment, the semi-rigid collar further includes a substantially flexible anti-slip portion having a pliant, non-resilient body.

In accordance with one or more aspects of the disclosed embodiment, wherein the semi-rigid collar includes substantially independent semi-rigid portions configured to effect substantially independent positioning of the occipital locking mechanisms on opposite sides against the base of the skull, wherein the substantially independent semi-rigid portions are joined by an articulated coupling.

In accordance with one or more aspects of the disclosed embodiment, the cervical collar further includes a wedge-shaped support pad contouring the base of the skull and effecting cervical traction generated by the traction mechanism.

In accordance with one or more aspects of the disclosed embodiment, a method for using a cervical collar includes applying the cervical collar to a neck, and providing a gap in the cervical collar maintaining an unobstructed clearance between the cervical collar and temporomandibular joint, jaw and chin of a skull, engaging a skull with an occipital locking mechanism of the cervical collar and the occipital locking mechanism being conformal to the mastoid or occipital region of the skull, generating a force with a traction mechanism coupled to the cervical collar, and maintaining the gap in the cervical collar, and transferring the force to the skull at the mastoid or occipital region with the occipital locking mechanism.

In accordance with one or more aspects of the disclosed embodiment, generating the force is effected by inflating the traction mechanism.

In accordance with one or more aspects of the disclosed embodiment, the method further includes leveraging the shoulders to transfer the force to the skull during inflation of the traction mechanism.

In accordance with one or more aspects of the disclosed embodiment, a cervical collar includes a semi-rigid collar, an occipital locking mechanism coupled to the semi-rigid collar, configured to conform to and engage with the base of a skull at only the occipital or mastoid region, and a traction mechanism coupled to the semi-rigid collar, the traction mechanism configured to provide cervical traction pressure to the occipital locking mechanism through the semi-rigid collar.

In accordance with one or more aspects of the disclosed embodiment, the semi-rigid collar has a gap which maintains an unobstructed clearance for the jaw, chin and temporomandibular region.

In accordance with one or more aspects of the disclosed embodiment, the gap is maintained during the actuation of the traction mechanism.

It should be understood that the aspects of the exemplary embodiment disclosed herein can be used individually or in any suitable combination thereof. It should also be understood that the foregoing description is only illustrative of the aspects of the disclosed embodiments. Various alternatives and modifications can be devised by those skilled in the art without departing from the aspects of the disclosed embodiments described herein. Accordingly, the present aspects of the disclosed embodiment are intended to embrace all such alternatives, modifications and variances that fall within the scope of the appended claims.

What is claimed is:

1. A cervical collar comprising:
   a semi-rigid collar substantially conforming to the back of a neck;

an occipital locking mechanism coupled to the semi-rigid collar, configured to generally conform to and engage with the base of a skull at the occipital or mastoid region via a closed front, the closed front at or below the horizontal level of the temporomandibular joint, without engaging the temporomandibular joint, jaw, chin, and front of the skull, front of a neck, and throat; and at least one traction mechanism coupled to the semi-rigid collar, the at least one traction mechanism configured to provide cervical traction through the occipital locking mechanism of the semi-rigid collar against the base of the skull without pressure of the cervical collar against the temporomandibular joint, jaw, chin, and front of the skull, front of the neck, and throat.

2. The cervical collar of claim 1, wherein the semi-rigid collar has a gap which maintains an unobstructed clearance between the cervical collar and the temporomandibular joint, jaw, chin, and front of the skull, front of the neck, and throat with the traction mechanism engaged to provide cervical traction.

3. The cervical collar of claim 2, further comprising a fastening system connected to the semi-rigid collar, wherein the fastening system is included in the closed front.

4. The cervical collar of claim 1, wherein the traction mechanism further comprises at least one inflatable bladder.

5. The cervical collar of claim 4, wherein the traction mechanism has a common inflation mechanism.

6. The cervical collar of claim 4, wherein the traction mechanism is configured to engage the shoulders at a base of the semi-rigid collar.

7. The cervical collar of claim 4, wherein the at least one inflatable bladder has at least one baffle configured to control inflation of the at least one inflatable bladder.

8. The cervical collar of claim 1, the semi-rigid collar further comprising a pliant, non-resilient coupling.

9. The cervical collar of claim 8, wherein the pliant coupling couples semi-rigid portions of the semi-rigid collar so that the coupled semi-rigid portions are substantially independent portions relative to each other configured so that engagement of the occipital locking mechanism with the skull is substantially independent engagement of each opposite side of the occipital locking mechanism with opposite sides of the base of the skull from a common cervical traction action of the at least one traction mechanism.

10. The cervical collar of claim 1, further comprising a wedge-shaped support pad contouring the base of the skull and effecting cervical traction generated by the traction mechanism.

11. The cervical collar of claim 1, wherein the closed front includes a front adjustable closure, and the size of the front adjustable closure can be linearly varied to increase or decrease the perimeter of the semi-rigid collar.

12. The cervical collar of claim 1, further comprising a rear adjustable closure, wherein the size of the rear adjustable closure can be varied to increase or decrease the size of the semi-rigid collar.

13. The cervical collar of claim 1, wherein the height of the semi-rigid collar can be linearly varied via an adjustment mechanism independent of the traction mechanism.

14. A cervical collar comprising:
a semi-rigid collar having an interior surface; the semi-rigid collar further having a gap which maintains an unobstructed clearance between the cervical collar and the temporomandibular joint, jaw, chin, and front of a skull, front of a neck, and throat;
an occipital locking mechanism on the semi-rigid collar, configured to generally conform to and engage with the base of the skull at the occipital or mastoid region via a closed front, the closed front at or below the horizontal level of the temporomandibular joint; and
a traction mechanism coupled to the semi-rigid collar, the traction mechanism configured to provide cervical traction through the occipital locking mechanism of the semi-rigid collar against the base of the skull;
wherein, the gap of the semi-rigid collar persists when the traction mechanism is engaged to provide cervical traction.

15. The cervical collar of claim 14, further comprising a fastening system connected to the semi-rigid collar, wherein the fastening system is included in the closed front.

16. The cervical collar of claim 14, wherein the traction mechanism further comprises at least one inflatable bladder.

17. The cervical collar of claim 16, wherein the traction mechanism has a common inflation mechanism.

18. The cervical collar of claim 16, wherein the at least one inflatable bladder has at least one baffle configured to control inflation of the at least one inflatable bladder.

19. The cervical collar of claim 14, further comprising a pliant, non-resilient body.

20. The cervical collar of claim 14, wherein the semi-rigid collar includes substantially independent semi-rigid portions configured to effect substantially independent positioning of the occipital locking mechanism on opposite sides against the base of the skull from a common cervical traction action of the at least one traction mechanism, wherein the substantially independent semi-rigid portions are joined by an articulated coupling.

21. A method for using a cervical collar comprising:
applying the cervical collar to a neck and providing a gap in the cervical collar maintaining an unobstructed clearance between the cervical collar and temporomandibular joint, jaw, chin, and front of a skull, front of a neck, and throat;
engaging a skull with an occipital locking mechanism of the cervical collar via a closed front, the closed front at or below the horizontal level of the temporomandibular joint, and the occipital locking mechanism being conformal to the mastoid and/or occipital region of the skull;
generating a force with a traction mechanism coupled to the cervical collar, and maintaining the gap in the cervical collar; and
transferring the force to the skull at the mastoid and/or occipital region with the occipital locking mechanism.

22. The method of claim 21, wherein generating the force is effected by inflating the traction mechanism.

23. The method of claim 22, further comprising leveraging the shoulders to transfer the force to the skull during inflation of the traction mechanism.

* * * * *